United States Patent [19]

Shimizu et al.

[11] Patent Number: 5,359,129

[45] Date of Patent: Oct. 25, 1994

[54] METHOD FOR PREVENTING COLORATION OF DIPHENYLMETHANE DIISOCYANATE COMPOUND

[75] Inventors: Masato Shimizu; Toshiaki Nakano, both of Amagasaki, Japan

[73] Assignee: Sumitomo Bayer Urethane Co. Ltd., Amagasaki, Japan

[21] Appl. No.: 167,506

[22] Filed: Dec. 15, 1993

[30] Foreign Application Priority Data

Dec. 24, 1992 [JP] Japan .................. 4-343991

[51] Int. Cl.$^5$ .................. C07C 265/14; C07D 211/00
[52] U.S. Cl. .................. 560/332; 560/330; 560/331; 546/222
[58] Field of Search .................. 560/330, 332, 331; 546/216, 222

[56] References Cited

U.S. PATENT DOCUMENTS

| | | | |
|---|---|---|---|
| 2,957,903 | 10/1960 | Spiegler | 260/453 |
| 4,340,533 | 7/1982 | Rody | 524/99 |
| 4,351,915 | 9/1982 | Kubota et al. | 524/103 |
| 4,452,884 | 6/1984 | Leppard | 430/551 |

FOREIGN PATENT DOCUMENTS 59-58022  4/1984  Japan .

OTHER PUBLICATIONS

AN 84-118563 & JP-A-59059 022 (Nippon Polyurethane KK) Abstract (1984).
Chemical Abstracts, vol. 117, No. 14, Oct. 5, 1992, Columbus, Ohio, US; abstract No. 131713s, Y. Oda et al. "Manufacture of ring-brominated styrene monomers" p. 10; abstract & JP-A-04 134 039 (Tosoh Corp.).
Chemical Abstracts, vol. 115, No. 18, Nov. 4, 1991, Columbus, Ohio, US; abstract No. 194288m, Y. Abe et al. 'Thermal recording material using piperidine derivative' p. 772; abstract and JP-A-03 069 392 (Oji Paper Co.).

*Primary Examiner*—Celia Chang
*Attorney, Agent, or Firm*—Joseph C. Gil

[57] ABSTRACT

A method for preventing the coloration of a diphenylmethane diisocyanate compound, which comprises adding, to the diphenylmethane diisocyanate compound, a hindered amine compound of the formula:

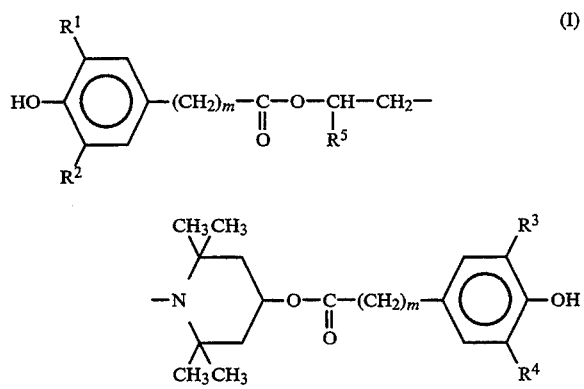

wherein
R$^1$ and R$^3$ are, the same or different, each a hydrogen atom or a C$_1$–C$_8$ hydrocarbon group,
R$^2$ and R$^4$ are, the same or different, each a C$_1$–C$_8$ hydrocarbon group,
R$^5$ is a hydrogen atom, a methyl group, an ethyl group, a phenoxymethyl group or a phenyl group, and
m is 0, 1 or 2, in an amount of 0.001 to 1.0 parts by weight per 100 parts by weight of the diphenylmethane diisocyanate compound.

An excellent effect of preventing the coloration can be achieved only by the addition of a small amount of the hindered amine compound of the formula (I).

1 Claim, No Drawings

METHOD FOR PREVENTING COLORATION OF DIPHENYLMETHANE DIISOCYANATE COMPOUND

The present invention relates to a method for preventing the coloration of a diphenylmethane diisocyanate compound caused by the air, light, heat or the like.

A diphenylmethane diisocyanate compound (referred to as "MDI compound" hereinafter) is used as a raw material for a polyurethane resin molded article, an artificial leather, a paint, an adhesive, a fiber and the like.

Although the MDI compound is colorless transparent or pale yellow immediately after its preparation, the MDI compound is colored when it is exposed to the air or light or heated during storage. The colored MDI compound cannot be used as the raw material for the artificial leather, paint, resin and the like having a white color. Therefore, the MDI compound is purified under a well-controlled condition, and a stabilizing agent such as an antioxidant or an ultraviolet light absorbing agent is added to the MDI compound to prevent the coloration during the storage.

Some methods for preventing the coloration of the MDI compound are proposed. A method comprising adding a hindered phenol such as 1,6-di-tert.-butyl-4-methylphenol (referred to as "BHT" hereinafter) or a phosphorous acid ester such as triphenyl phosphite (referred to as "TPP" hereinafter) is disclosed in U.S. Pat. No. 2,957,903. A method comprising adding a hindered amine compound such as bis(1,2,2,6,6-pentamethyl-4-piperidyl) sebacate is disclosed in Japanese Patent Kokai Publication No. 58022/1984.

However, an sufficiently excellent effect of preventing the coloration cannot be achieved by the above methods. In particular, in the case of the MDI compound which is in solid or semi-molten state at a room temperature, the MDI compound is usually stored in a solid state at a low temperature or a liquid state by warming. Since the MDI compound is repeatedly solidified and molten prior to the use, it is more liable to color. When the MDI compound is reacted with various polyols and amines having active hydrogens, a reaction controlling agent is often added to a reaction mixture, because a reaction rate is so high that the reaction is hardly controllable depending on the kind of the reactants or reaction conditions. In this case, the use of the controlling agent is limited because the coloration becomes worse.

An amount of the stabilizing agent added to the MDI compound is usually large, for example, 0.03–0.20% by weight based on the MDI compound. In addition, only one stabilizing agent cannot give a practically satisfactory effect of preventing the coloration.

An object of the present invention is to provide a method for preventing the coloration of a MDI compound, which gives a excellent effect of preventing the coloration with a small addition amount of a stabilizing agent.

The present invention relates to a method for preventing the coloration of a MDI compound, which comprises adding, to the MDI compound, a hindered amine compound of the formula:

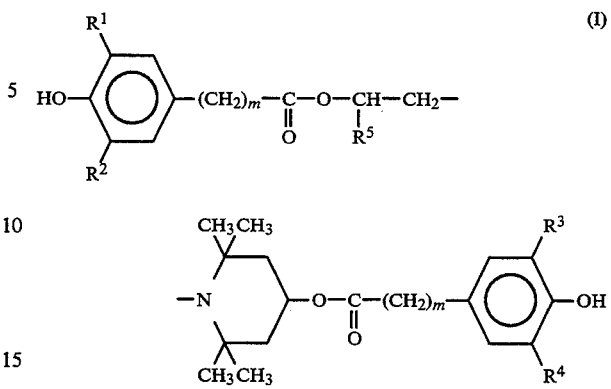

wherein
$R^1$ and $R^3$ are, the same or different, each a hydrogen atom or a $C_1$–$C_8$ hydrocarbon group,
$R^2$ and $R^4$ are, the same or different, each a $C_1$–$C_8$ hydrocarbon group,
$R^5$ is a hydrogen atom, a methyl group, an ethyl group, a phenoxymethyl group or a phenyl group, and
m is 0, 1 or 2,
in an amount of 0.001 to 1.0 parts by weight per 100 parts by weight of the MDI compound.

Specific examples of the MDI compound are
(a) diphenylmethane-4,4'-diisocyanate, and a mixture thereof with other isomers of diphenylmethane diisocyanate,
(b) a polymer and oligomer (referred to as "MDI prepolymer" hereinafter) prepared by reacting diphenylmethane diisocyanate with an isocyanate-reactive compound (for example, a diol, polyol or a mixture thereof, or a polyester or polyether having a terminal hydroxyl or amino group), and
(c) modified diphenylmethane diisocyanate (in which some of isocyanate groups were converted to other functional groups such as carbodiimide, isocyanurate and uretoneimine groups).

In the hindered amine compound of the formula (I), $R^1$ and $R^3$ are preferably tert.-butyl groups, and $R^2$ and $R^4$ are preferably tert.-butyl groups.

Specific examples of the hindered amine compound of the formula (I) are as follows:

(1)  1-[2-[3-(3,5-di-tert.-butyl-4-hydroxyphenyl)propionyloxy]ethyl]-4-[3-(3,5-di-tert.-butyl-4-hydroxyphenyl)propionyloxy]-2,2,6,6-tetramethylpiperidine, (2)  1-[2-[2-(3,5-di-tert.-butyl-4-hydroxyphenyl)acetyloxy]ethyl]-4-[2-(3,5-di-tert.-butyl-4-hydroxyphenyl)acetyloxy]-2,2,6,6-tetramethylpiperidine, (3) 1-[2-(3,5-di-tert.-butyl-4-hydroxybenzoyloxy)ethyl]-4-(3,5-di-tert.-butyl-4-hydroxybenzoyloxy)-2,2,6,6-tetramethylpiperidine, (4)  1-[2-[3-(3,5-di-tert.-butyl-4-hydroxyphenyl)propionyloxy]-2-methylethyl]-4-[3-[3,5-di-tert.-butyl-4-hydroxyphenyl)propionyloxy]-2,2,6,6-tetramethylpiperidine, (5)  1-[2-[3-(3,5-di-tert.-butyl-4-hydroxyphenyl)propionyloxy]-2-ethylethyl]-4-[3-3,5 -di-tert.-butyl-4-hydroxyphenyl)propionyloxy]-2,2,6,6-tetramethylpiperidine, and (6)  1-[2-[3-(3,5-di-tert.-butyl-4-hydroxyphenyl)propionyloxy]-2-phenylethyl]-4-[3-(3,5-di-tert.-butyl-4- hydroxyphenyl)propionyloxy]-2,2,6,6-tetramethyl-piperidine.

The hindered amine compound (1) is particularly preferable.

An addition amount of the hindered amine compound of the formula (I) varies depending on the kind of the MDI compound and the composition, but is usually 0.001 to 1.0 parts by weight, preferably from 0.001 to 0.1 parts by weight, more preferably 0.001 to 0.03 parts by weight based on 100 parts by weight of the MDI compound.

When the MDI compound is a product prepared by a reaction of diphenylmethane diisocyanate, the hindered amine compound (I) is preferably added to diphenylmethane diisocyanate before conducting the reaction.

In the present invention, an additive, for example, an antioxidant such as BHT and a hindered amine compound such as bis(1,2,2,6,6-pentamethyl-4-piperidyl) sebacate may be added in addition to the hindered amine compound of the formula (I).

When the MDI compound is reacted, a reaction controlling agent, for example, an aromatic carboxylic acid chloride such as benzoyl chloride and isophthalic acid chloride, an inorganic acid such as hydrochloric acid and phosphoric acid, and an aliphatic carboxylic acid such as acetic acid and propionic acid may be added. An addition amount of the reaction controlling agent varies depending on the kinds of the MDI compound and the isocyanate-reactive compound and the reaction conditions, but is usually from 1 to 300 ppm based on the MDI compound. The hindered amine compound of the formula (I) and the reaction controlling agent can be added in any conventional manner.

EXAMPLES

The present invention is illustrated by following Examples.

Example 1

A hindered amine compound (1) [a hindered amine compound wherein $R^1$–$R^4$ are tert.-butyl groups, $R^5$ is a hydrogen atom and m is 2 in the formula (I)] in an amount shown in Table 1 as a stabilizing agent was added to purified diphenylmethane diisocyanate (APHA value: 5). The mixture was solidified by rapidly cooling to −15° C. under a nitrogen gas atmosphere. After two days, the mixture was liquefied by warming to 50° C. and an APHA value was measured.

Tests by using a sample without the addition of the stabilizing agent, samples with the addition of BHT, TPP and bis(1,2,2,6,6-pentamethyl-4-piperidyl) sebacate (referred to as "LS-765" hereinafter), respectively, as the stabilizing agent and a sample with the addition of a mixture of BHT and LS-765 were conducted for comparison. The results are shown in Table 1.

TABLE 1

| Stabilizing agent | Addition amount (ppm) | APHA value After 2 days at −15° C. |
| --- | --- | --- |
| Hindered amine compound (1) | 70 | 10 |
|  | 100 | 10 |
| No addition | 0 | 400 |
| BHT | 100 | 200 |
| TPP | 100 | 200 |
| LS-765 | 100 | 100 |
| BHT + LS-765 | 60 + 40 | 180 |

Example 2

The tests were conducted in the same as in Example 1, except that benzoyl chloride was added as a reaction controlling agent in an amount of 25 ppm based on the weight of diphenylmethane diisocyanate, immediately after the addition of the stabilizing agent shown in Table 2 to purified diphenylmethane diisocyanate (APHA value: 5). The results are shown in Table 2.

TABLE 2

| Stabilizing agent | Addition amount (ppm) | APHA value After 2 days at −15° C. |
| --- | --- | --- |
| Hindered amine compound (1) | 100 | 20 |
| No addition | 0 | 500 |
| BHT | 100 | 300 |
| TPP | 100 | 300 |
| LS-765 | 100 | 150 |
| BHT + LS-765 | 60 + 40 | 180 |

Example 3

A MDI prepolymer (isocyanate group content: 22.9%) prepared by adding a stabilizing agent in an amount shown in Table 3 to purified diphenylmethane diisocyanate (APHA value: 5) and then reacting stabilized diphenylmethane diisocyanate with tripropylene glycol. After the MDI prepolymer was warmed to 60° C. and stirred for three hours, its APHA value was measured. In addition, a test with adding benzoyl chloride (25 ppm) as a reaction controlling agent immediately after the addition of the stabilizing agent was also conducted.

Tests by using a sample without the addition of the stabilizing agent, samples with the addition of BHT, TPP and LS-765, respectively, as the stabilizing agent and a sample with the addition of a mixture of BHT and LS-765 were conducted for comparison. The results are shown in Table 3.

TABLE 3

| Stabilizing agent | Addition amount (ppm) | APHA value without benzoyl chloride | APHA value with benzoyl chloride |
| --- | --- | --- | --- |
| Hindered amine compound (1) | 100 | 20 | 20 |
| No addition | 0 | 50 | 70 |
| BHT | 100 | 20 | 30 |
| TPP | 100 | 35 | 50 |
| LS-765 | 100 | 40 | 60 |
| BHT + LS-765 | 60 + 40 | 30 | 50 |

An excellent effect of preventing the coloration can be achieved only by the addition of a small amount of the hindered amine compound of the formula (I) as the stabilizing agent. The coloration prevention effect is excellent even with an additive such as a reaction controlling agent.

What is claimed is:

1. A method for preventing the coloration of a diphenylmethane diisocyanate compound, which comprises adding, to the diphenylmethane diisocyanate compound, a hindered amine compound of the formula:

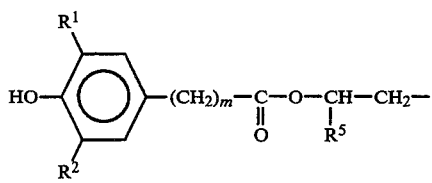
(I)
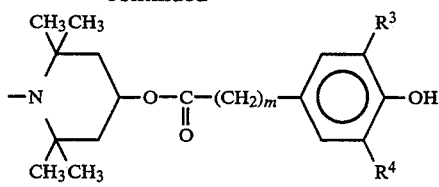
wherein
R¹ and R³ are, the same or different, each a hydrogen atom or a $C_1$-$C_8$ hydrocarbon group,
R² and R⁴ are, the same or different, each a $C_1$-$C_8$ hydrocarbon group,
R⁵ is a hydrogen atom, a methyl group, an ethyl group, a phenoxymethyl group or a phenyl group, and
m is 0, 1 or 2,
in an amount of 0.001 to 1.0 parts by weight per 100 parts by weight of the diphenylmethane diisocyanate compound.
* * * * *